United States Patent [19]

Christidis et al.

[11] 4,402,978
[45] Sep. 6, 1983

[54] GASTRO-PROTECTING ACTIVITY OF SUBSTITUTED DERIVATIVES OF 4-PHENYL-4-OXO-2-HYDROXY-BUTANOIC ACID

[75] Inventors: Yani Christidis; Robert Fournex, both of Paris; Colette Tournemine, Livry-Gargan, all of France

[73] Assignee: Roussel-Uclaf, Romainville, France

[21] Appl. No.: 256,911

[22] Filed: Apr. 23, 1981

[30] Foreign Application Priority Data

Apr. 24, 1980 [FR] France .................. 80 09215

[51] Int. Cl.³ .................. A61K 31/19; A61K 31/235; A61K 31/24
[52] U.S. Cl. .................. 424/317; 424/308; 424/309; 424/282
[58] Field of Search .................. 424/308, 309, 317, 282

[56] References Cited

U.S. PATENT DOCUMENTS

| | | | |
|---|---|---|---|
| 2,532,579 | 12/1950 | Thomas | 167/22 |
| 2,562,208 | 7/1951 | Papa et al. | 167/30 |
| 3,753,997 | 8/1973 | Ash et al. | 260/296 R |
| 3,763,148 | 10/1973 | Ash et al. | 260/295 R |
| 3,846,470 | 11/1974 | Raube et al. | 260/465 E |
| 3,910,959 | 10/1975 | Vallet | 260/340.5 |
| 3,940,404 | 2/1976 | Ash et al. | 260/296 R |
| 3,940,487 | 2/1976 | La Croix et al. | 424/282 |
| 3,953,463 | 4/1976 | Ash et al. | 260/295 R |
| 4,017,517 | 4/1977 | Murata et al. | 260/340.5 |

FOREIGN PATENT DOCUMENTS

| | | | |
|---|---|---|---|
| 1282644 | 9/1962 | Fed. Rep. of Germany . | |
| 2047806 | 4/1972 | Fed. Rep. of Germany . | |
| 2103749 | 8/1972 | Fed. Rep. of Germany | 424/317 |
| 2501834 | 7/1975 | Fed. Rep. of Germany . | |
| 1566213 | 5/1969 | France . | |
| 1566212 | 7/1973 | France . | |
| 2132354 | of 0000 | France . | |
| 2270856 | of 0000 | France . | |
| 55-36434 | 3/1980 | Japan . | |
| 591415 | 9/1977 | Switzerland . | |
| 588108 | 6/1947 | United Kingdom . | |
| 1387733 | 3/1975 | United Kingdom | 424/317 |

OTHER PUBLICATIONS

*Journal of American Pharmaceutical Association*, vol. 37, No. 11, Nov. 1948, pp. 439–449.
*Chemical Abstracts*, vol. 88, No. 5, Jan. 30, 1978 Abstract 37442p.
*Journal of the American Chemical Society*, vol. 71, No. 4, Apr. 1949, F. K. Kirchner et al., pp. 1210–1213.
*Journal of the American Chemical Society*, vol. 70, No. 10, Oct. 1948, D. Papa et al., pp. 3356–3360.
*European Journal of Medical Chemistry Chimica Therapeutica*, vol. 12, Jan.–Feb. 1977, pp. 17–20.
*European Journal of Medical Chemistry Chimica Therapeutica*, vol. 13, No. 3, May–Jun. 1978, H. Orzalesi et al., pp. 259–264.
*Beilstein*, vol. 19, p. 312.
*Journal of Pharmaceutical Sciences*, vol. 66, No. 4, Apr. 1977, pp. 466–476, Child, Ralph G., et al., "Fenbufen, a New Anti-Inflammatory Analgesic: Synthesis and Structure—Activity Relationships of Analogs".
*Journal of Medicinal Chemistry*, vol. 15, No. 9, Sep. 1972, pp. 918–922, Markovac, A., et al.,—"Antimalarials 3, 2,6-Bis(aryl)-4-pyridinemethanols with Trifluoromethyl Substituents".
*Journal of Organic Chemistry*, vol. 35, No. 5, May 1970, pp. 1367–1376, Pettit, George R., et al., "Bufadienolides 1., Introduction and Base-Catalyzed Condensation of Methyl Ketonds with Glyoxylic Acid".
*J.A.C.S.*, vol. 46, No. 10, Oct. 1924, pp. 2319–2326 Rice, Grace Potter, "The Isomeric Esters of Para-Ethoxy-Benzoylacrylic Acid".

*Primary Examiner*—Frederick E. Waddell
*Attorney, Agent, or Firm*—Stevens, Davis, Miller & Mosher

[57] ABSTRACT

Diseases and ailments accompanied by gastric and gastroduodenal lesions treated by administering a compound of the formula (I)

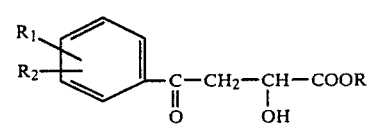

(I)

in which R represents hydrogen or alkyl containing 1 to 5 carbon atoms and $R_1$ and $R_2$, identical or different, both represent alkoxy containing 1 to 3 carbon atoms, or both represent halogen, or $R_1$ represents hydrogen and $R_2$ represents halogen, nitro or trifluoromethyl, or $R_1$ and $R_2$ form a methylenedioxy group at adjacent carbon atoms, in their racemic and optically active forms, as well as pharmaceutically acceptable salts thereof, particularly alkali metal, alkaline earth metal, or amine salts of said acid.

20 Claims, No Drawings

GASTRO-PROTECTING ACTIVITY OF SUBSTITUTED DERIVATIVES OF 4-PHENYL-4-OXO-2-HYDROXY-BUTANOIC ACID

The present invention relates to the treatment of diseases and ailments accompanied by gastric and gastroduodenal lesions by administering certain substituted derivatives of 4-phenyl-4-oxo-2-hydroxy-butanoic acid which exhibit gastric acid secretion inhibiting and cytoprotecting activity, and to pharmaceutical compositions containing those compounds.

More particularly, the present invention relates to inhibiting gastric acid secretion with compounds represented by the formula (I)

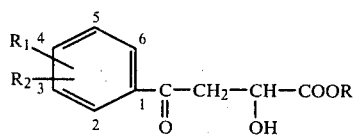

in which R represents hydrogen or alkyl containing 1 to 5 carbon atoms and $R_1$ and $R_2$, identical or different, both represent alkoxy containing 1 to 3 carbon atoms, or both represent halogen, or $R_1$ represents hydrogen and $R_2$ represents halogen, nitro or trifluoromethyl, or $R_1$ and $R_2$ form a methylenedioxy group at adjacent carbon atoms, in their racemic and optically active forms, as well as pharmaceutically acceptable salts thereof, particularly alkali metal, alkaline earth metal, or amine salts of said acid.

Some of these compounds are known in the art, as for example 4-(2,5-dimethoxyphenyl)-4-oxo-2-hydroxybutanoic acid disclosed by Pettit et al., J. Org. Chem., 1970, Vol. 35, No. 5, pp. 1367–1376. The gastro-protecting effect of such compounds has not heretofore been reported.

Preferred compounds of formula (I) are those wherein R is as defined above, $R_1$ and $R_2$, identical or different, both represent alkoxy containing 1 to 3 carbon atoms, or both represent halogen, or $R_1$ represents hydrogen and $R_2$ represents halogen, nitro group, or trifluoromethyl, in their racemic or optically active forms, as well as the pharmaceutically acceptable alkali metal, alkaline earth metal, or amine salts of said compounds in which R represents hydrogen.

The term "alkyl containing 1 to 5 carbon atoms", includes, for example, methyl, ethyl, n-propyl, isopropyl, n-butyl, isobutyl, tert.-butyl and pentyl.

The term "alkoxy containing 1 to 3 carbon atoms" includes, for example, methoxy, ethoxy, n-propoxy and isopropoxy.

The term "halogen atom" includes, for example, chlorine, bromine and fluorine.

The alkali metal or alkaline earth metal salts of compounds of formula (I) in which R represents a hydrogen atom include, for example, sodium salts, potassium salts, lithium salts and calcium salts.

The amine salts of compounds of formula (I), in which R represents a hydrogen atom, are the usual amine salts. Among the usual amines, there can be mentioned the monoalkylamines, such as, for example, methylamine, ethylamine, propylamine; the dialkylamines, such as, for example, dimethylamine, diethylamine, di-n-propylamine; and, trialkylamines, such as, triethylamine. There can likewise be mentioned piperidine, morpholine, piperazine and pyrrolidine.

More preferred compounds of formula (I) are those wherein $R_1$ and $R_2$, identical or different, both represent alkoxy containing 1 to 3 carbon atoms, or both represent halogen, or $R_1$ represents hydrogen and $R_2$ represents halogen or nitro in their racemic and optically active forms, as well as the pharmaceutically acceptable alkali metal, alkaline earth metal, or amine salts of the said formula (I) in which R represents hydrogen.

Most preferred of the just mentioned compounds and salts of formula (I) are trhose wherein $R_1$ and $R_2$, identical or different, both represent alkoxy containing 1 to 3 carbon atoms, or both represent halogen, or $R_1$ represents hydrogen and $R_2$ represents halogen.

As illustrative of the above compounds, there is mentioned in particular 4-(3,4-dimethoxyphenyl)-4-oxo-2-hydroxybutanoic acid and 4-(3,5-dimethoxyphenyl)-4-oxo-2-hydroxybutanoic acid.

The compounds of formula (I) above and their salts can be prepared by a process according to which a compound of formula (II):

in which R is as defined before is caused to react with an acetophenone of formula (III):

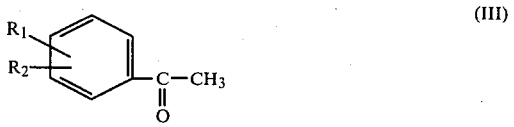

in which $R_1$ and $R_2$ have the meaning defined above, to obtain a corresponding product of formula (I) which, if desired, is converted into a salt or ester by the usual methods.

Under the preferred conditions of operation, the process described above is carried out in the following manner:

Condensation of the product of formula (II) and the product of formula (III) is carried out at a temperature between 60° C. and 120° C. using an excess of the product of formula (III). However, when the product of formula (II) in which R represents hydrogen is used, the operation can be carried out with equal advantage at room temperature in the presence of a catalyst such as an alkaline agent (sodium hydroxide, potassium hydroxide, for example).

The operation can likewise be carried out in the presence of a solvent such as an aromatic or aliphatic hydrocarbon (benzene, toluene, heptane, for example).

The products of formula (I) above, in which R represents hydrogen, can likewise be prepared by a process according to which a product of formula (IV):

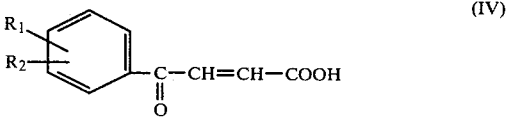

in which $R_1$ and $R_2$ have the value indicated above, is condensed with water in an acid medium.

Under preferred conditions of carrying out the latter process, the operation is as follows:

Hydration is carried out at a temperature ranging from 60° C. to the reflux temperature of the reaction medium. The acid utilized can be, for example, hydrochloric acid, sulfuric acid, or phosphoric acid.

The alkali metal, alkaline earth metal, or amine salts of the products of formula (I) can be prepared in the usual manner, by reaction of the said products of formula (I) with the corresponding bases.

The above described compounds according to the invention are very useful in human therapy, particularly for the treatment of hyperchlorhydria, gastric ulcers, gastroduodenal ulcers, gastritis, hiatal hernias, and gastroduodenal diseases accompanied by gastric hyperacidity.

Dosage, which is variable according to the specific product utilized and the disease in question, can range, for example, between 0.05 and 2 g, preferably between 0.2 g and 1.5 g per day in adults via oral administration.

A further object of the present invention is to provide pharmaceutical compositions which contain, as the active ingredient, at least one of the above-mentioned compounds. These compositions are prepared so as to be administrable by the digestive or parenteral route.

They can be solid or liquid and can be embodied in the pharmaceutical forms at present utilized in human medicine, such as, for example, simple or coated tablets, capsules, granules, suppositories, or injectable preparations, all of which can be prepared by the usual methods.

The active principle or principles can be incorporated in excipients usually used in these pharmaceutical compositions such as talc, gum arabic, lactose, starch, magnesium stearate, cocoa butter, aqueous or non-aqueous vehicles, fatty materials of animal or vegetable origin, paraffinic derivatives, glycols, various wetting agents, dispersants or emulsifiers, and preservatives.

The examples presented below are for the purpose of illustrating the invention without, however, limiting it to these specific embodiments.

EXAMPLE 1

4-(3,4-dimethoxyphenyl)-4-oxo-2-hydroxy-butanoic acid 22.2 g of glyoxylic acid, 50% by weight in water, are heated under reduced pressure until about 80% of the water present is eliminated; then, after cooling, 54 g of 3,4-dimethoxyacetophenone are introduced into the reaction medium, i.e., a 100% excess over theoretical.

Heating is performed for 150 minutes at 95° C. under reduced pressure, the water present being simultaneously distilled off.

Then, after cooling of the medium to room temperature, there are introduced 60 cm$^3$ of ether and 100 cm$^3$ of distilled water containing 8.7 g of pure, dry sodium carbonate.

After decantation, the organic phase is washed with ether, then the united aqueous phases are acidified to pH 1 with 6 N hydrochloric acid. The desired product is then extracted with ethyl acetate. After washing, drying and elimination of the extraction solvent under vacuum, 37 g of the desired product are isolated in the form of an oil, which crystallizes spontaneously on cooling.

After recrystallization in 1,2-dichloroethane, there are obtained 19.7 g of 4-(3,4-dimethoxyphenyl)-4-oxo-2-hydroxybutanoic acid.

m.p. = 107 ± 1° C.

|  | Analysis | |
|---|---|---|
|  | C % | H % |
| Calculated | 56.69 | 5.55 |
| Found | 56.5 | 5.5 |

NMR Spectrum:

The product was analyzed in solution in $D_6$ acetone with trimethylsilane as the reference material.

The chemical displacements of protons in the groups —CH$_2$—CH(OH)— and —OCH$_3$ are given below: S = 3.35 ppm, d, 2H, J = 6 Hz; S = 3.8 ppm, 2S, 6H; S = 4.66 ppm, t, 1H, J = 6 Hz.

Acidimetry (expressed as percentage of theoretical) = 98.8%.

By the action of diazomethane on the product obtained above, 4-(3,4-dimethoxyphenyl)-4-oxo-2-hydroxy-butanoic acid, there was obtained methyl 4-(3,4-dimethoxyphenyl)-4-oxo-2-hydroxy-butanoate.

m.p. = 103 ± 1° C.

|  | Analysis ($C_{13}H_{16}O_6$) | |
|---|---|---|
|  | C % | H % |
| Calculated: | 58.20 | 6.01 |
| Found: | 58.1 | 6.1 |

EXAMPLES 2–12

The products of the following Examples 2–12 were prepared by proceeding in the manner described in Example 1, starting from glyoxylic acid and an acetophenone correspondingly substituted in the phenyl nucleus. The products and their characteristics are set forth in the following Tables 1 and 2.

TABLE 1

| Example No. | Product | Empirical formula | Molecular weight | m.p. and recrystallization solvent* |
|---|---|---|---|---|
| 2 | 4-(4-chlorophenyl)-4-oxo-2-hydroxy-butanoic acid | $C_{10}H_9ClO_4$ | 228.6 | 137° C. (a) |
| 3 | 4-(3,4-dichlorophenyl)-4-oxo-2-hydroxy-butanoic acid | $C_{10}H_8Cl_2O_4$ | 263.1 | 146° C. (b) |
| 4 | 4-(2,4-dichlorophenyl)-4-oxo-2-hydroxy-butanoic acid | $C_{10}H_8Cl_2O_4$ | 263.1 | 77° C. (a) |
| 5 | 4-(4-bromophenyl)-4-oxo-2-hydroxy-butanoic acid | $C_{10}H_9BrO_4$ | 273.1 | 149° C. (c) |
| 6 | 4-(4-fluorophenyl)-4-oxo-2-hydroxy-butanoic acid | $C_{10}H_9FO_4$ | 212.2 | 127° C. (a) |
| 7 | 4-(3-nitrophenyl)-4-oxo-2-hydroxy-butanoic acid | $C_{10}H_9NO_6$ | 239.2 | 138° C. (b) |
| 8 | 4-(4-nitrophenyl)-4-oxo-2-hydroxy-butanoic acid | $C_{10}H_9NO_6$ | 239.2 | 108° C. (b) |

TABLE 1-continued

| Example No. | Product | Empirical formula | Molecular weight | m.p. and recrystallization solvent* |
|---|---|---|---|---|
| 9 | 4-(2,4-dimethoxyphenyl)-4-oxo-2-hydroxybutanoic acid | $C_{12}H_{14}O_6$ | 254.24 | 106° C. (a) |
| 10 | 4-(2,5-dimethoxyphenyl)-4-oxo-2-hydroxy-butanoic acid | $C_{12}H_{14}O_6$ | 254.24 | 89° C. (a) |
| 11 | 4-(3,5-dimethoxyphenyl)-4-oxo-2-hydroxy-butanoic acid | $C_{12}H_{14}O_6$ | 254.24 | 119° C. (a) |
| 12 | 4-(4-trifluoromethylphenyl)-4-oxo-2-hydroxy-butanoic acid | $C_{11}H_9F_3O_4$ | 262.18 | 119° C. (a) |

*Recrystallization solvents:
(a) = 1,2-dichloroethane,
(b) = ethyl acetate,
(c) = methyl ethyl ketone

TABLE 2

| Example No. | Elemental Analyses Found (calculated) | Acidimetry expressed as % of theory | NMR** |
|---|---|---|---|
| 2 | C % 52.6 (52.53) H % 4.0 (3.97) Cl % 15.6 (15.51) | 98.5% | S = 3.45 ppm, d, 2H, J = 6Hz<br>S = 4.7 ppm, t, 1H, J = 6Hz |
| 3 | C % 45.5 (45.65) H % 3.1 (3.07) Cl % 26.8 (26.95) | 99.2% | |
| 4 | C % 45.7 (45.65) H % 3.0 (3.07) Cl % 26.8 (26.95) | 100% | |
| 5 | C % 44.1 (43.98) H % 3.4 (3.32) Br 29.2 (29.26) | 99% | |
| 6 | C % 56.7 (56.61) H % 4.3 (4.28) | 98.8% | |
| 7 | C % 50.2 (50.22) H % 3.8 (3.79) N % 5.9 (5.86) | 99.6% | |
| 8 | C % 50.3 (50.22) H % 3.9 (3.79) N % 5.8 (5.86) | 98.7% | |
| 9 | C % 56.7 (56.69) H % 5.65 (5.55) | 99.3% | |
| 10 | C % 56.5 (56.69) H % 5.4 (5.55) | 100% | |
| 11 | C % 56.0 (56.69) H % 5.5 (5.55) | 98.9% | |
| 12 | C % 50.4 (50.39) H % 3.5 (3.46) | 99.3% | S = 3.52 ppm, d, 2H, J = 6Hz<br>S = 4.7 ppm, t, 1H, J = 6Hz |

**NMR Spectrum: The products were analyzed in solution in acetone with trimethylsilane as the reference material. The chemical displacements of protons in the —$CH_2$—CH(OH)— group are given.

EXAMPLE 13

4-(2-nitrophenyl)-4-oxo-2-hydroxy-butanoic acid 4-(2-nitrophenyl)-4-oxo-2-butenoic acid is hydrolyzed in solution in 80 volumes of about 2 N hydrochloric acid under reflux for 24 hours.

m.p.=108° C. (crystallization in 1,2-dichloroethane).

| | Analysis: | | |
|---|---|---|---|
| | C % | H % | N % |
| Calculated: | 50.22 | 3.79 | 5.86 |
| Found: | 50.1 | 3.8 | 5.7 |

Acidimetry (expressed as percentage of theoretical)=98.8%

EXAMPLE 14

4-(3,4-methylenedioxyphenyl)-4-oxo-2-hydroxy-butanoic acid 29.6 g (0.2 M) of glyoxylic acid, 50% in water, are heated under reduced pressure until about 80% of the water present has been eliminated; then, after cooling, 65.5 g (0.4 M) of 3′, 4′-methylenedioxyacetophenone are introduced into the reaction medium. Heating is performed for 3 hours at 95° C. under reduced pressure, the residual water present being simultaneously distilled off. After the medium has been cooled, there are introduced 200 cm³ of chloroform and 400 cm³ of water containing 12 g of sodium carbonate.

After decantation, the aqueous phase is washed with chloroform, then acidified to pH 1 with 6 N hydrochloric acid. After filtering and drying, there are obtained 20.6 g of the expected product.

m.p.=159° C.

| Analysis ($C_{11}H_{10}O_6$) = 238.2 | | |
|---|---|---|
| | C % | H % |
| Calculated: | 55.47 | 4.23 |
| Found: | 55.6 | 4.3 |

EXAMPLE 15

Pharmaceutical Forms (a) Tablets

Tablets were prepared corresponding to the following formulation:

| | |
|---|---|
| 4-(3,4-dimethoxyphenyl-4-oxo-2-hydroxy-butanoic acid | 100 mg |
| Excipient q.s. for a finished tablet to | 300 mg |
| (details of excipient: lactose, wheat starch, treated starch, rice starch, magnesium stearate, talc). | |

(b) Capsules

Capsules were prepared corresponding to the following formulation:

| | |
|---|---|
| 4-(4-fluorophenyl)-4-oxo-2-hydroxy-butanoic acid | 100 mg |
| Excipient q.s. for a finished capsule to | 300 mg |
| (details for excipient: talc, magnesium sterate, aerosil) | |

PHARMACOLOGICAL STUDY

(1) Determination of anti-ulcer activity

The method used is described by Shay et al. in Gastroenterology, 5, 43, (1945).

The Shay method consists of inducing ulcers in rats in the stomach region by pyloric ligation.

The animals are anesthetized with ether. A longitudinal incision is made, 1 cm below the sternum; the glandular part of the stomach and the duodenum are exposed, and a ligature is placed several mm below the pylorus. The muscular sheet is left as it is and the skin is sutured with 2 clips.

The animals immediately receive the dispersive or the substance to be studied, via the mouth, in a volume of 0.5 ml/100 g and are kept without food or drink until sacrificed, 16 hours after the treatment, by carotid bleeding.

Before removal of the stomach, a ligature is placed above the cardia.

The gastric liquid is collected for measurement of pH.

The stomach is then opened along the major curvature, rinsed with physiological serum, and spread out on millimeter graph paper to be examined under a binocular magnifier.

The severity of the lesions, graded 0 to 4, is macroscopically evaluated for each stomach.

For each group of rats, the mean intensity of the ulcerations is determined, and the protection is calculated as the ratio of the mean index for the treated group to the mean index for the control group.

The pH values of the gastric liquid are likewise determined for the treated and control animals.

The results obtained are reported in the following Table 3.

TABLE 3

| Product of Example | Dose (mg/kg) | pH of gastric liquid treated animals | pH of gastric liquid control animals | Ulcerations % of protection with respect to controls |
|---|---|---|---|---|
| 1 | 20 | 2.3 | 3.4 | 72% |
| | 4 | 3.0 | 2.8 | 72% |
| | 0.8 | 3.4 | 2.8 | 27% |
| 2 | 20 | 3.0 | 3.4 | 72% |
| | 4 | 3.5 | 2.8 | 25% |
| 3 | 100 | 4.2 | 2.3 | 91% |
| | 20 | 3.2 | 2.8 | 36% |
| 4 | 100 | 4.4 | 2.3 | 91% |
| | 20 | 2.9 | 2.8 | 9% |
| 5 | 100 | 3.4 | 2.3 | 95% |
| | 20 | 3.1 | 3.4 | 40% |
| 8 | 100 | 3.0 | 2.3 | 49% |
| 11 | 100 | 3.0 | 2.0 | 88% |
| | 20 | 2.0 | 1.8 | 60% |
| | 4 | 2.0 | 2.6 | 50% |
| | 1 | 1.9 | 2.2 | 53% |

(2) Determination of Acute Toxicity

The lethal dose $LD_{50}$ of the derivatives of certain examples were evaluated after administration by the oral route in mice.

The following results obtained are set forth in the following Table 4.

TABLE 4

| Product of Example | $LD_{50}$ (mg/kg) |
|---|---|
| 1 | >1000 |
| 2 | >1000 |
| 3 | >1000 |
| 4 | >1000 |
| 5 | >1000 |
| 8 | >1000 |
| 11 | >1000 |
| 13 | >1000 |

The above examples are illustrative of the invention, but are not to be deemed limitative. It is obvious to one skilled in the art that equivalent techniques and modifications may be employed without departing from the spirit of the invention and the scope of the appended claims.

What is claimed is:

1. A pharmaceutical composition comprising as the active ingredient a gastric acid secretion inhibiting and cytoprotecting effective amount of a compound selected from the group consisting of a substituted derivative of 4-phenyl-4-oxo-2-hydroxy-butanoic acid of the formula (I)

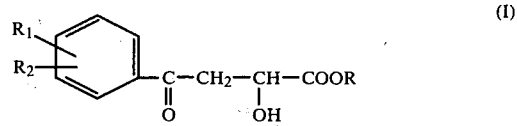

in which R represents hydrogen or alkyl group containing 1 to 5 carbon atoms and $R_1$ and $R_2$, identical or different, both represent alkoxy containing 1 to 3 carbon atoms, or both represent halogen, or $R_1$ represents hydrogen and $R_2$ represents halogen, nitro or trifluoromethyl, or $R_1$ and $R_2$ form a methylenedioxy group at adjacent carbon atoms, in their racemic or optically active forms, and pharmaceutically acceptable salts of said acid and a pharmaceutically acceptable carrier.

2. The composition according to claim 1, wherein R is as defined in claim 1 and $R_1$ and $R_2$ both represent alkoxy containing 1 to 3 carbon atoms, or both represent halogen, or $R_1$ represents hydrogen and $R_2$ represents halogen, nitro or a trifluoromethyl group.

3. The composition according to claim 2, wherein $R_1$ and $R_2$, identical or different, both represent alkoxy containing 1 to 3 carbon atoms, or both represent halogen, or $R_1$ represents hydrogen and $R_2$ represents halogen or nitro.

4. The composition according to claim 2, wherein $R_1$ and $R_2$, identical or different, both represent alkoxy containing 1 to 3 carbon atoms, or both represent halogen, or $R_1$ represents hydrogen and $R_2$ represents halogen.

5. The composition according to claim 2, wherein $R_1$ and $R_2$, identical or different, both represent alkoxy containing 1 to 3 carbon atoms.

6. The composition according to claim 1, 2, 3, 4 or 5, wherein said pharmaceutically acceptable salts are selected from the group consisting of alkali metal, alkaline earth metal and amine salts.

7. The composition according to claim 1, wherein the compound is 4-(3,4-dimethoxyphenyl)-4-oxo-2-hydroxy-butanoic acid.

8. The composition according to claim 1, wherein the compound is 4-(3,5-dimethoxyphenyl)-4-oxo-2-hydroxy-butanoic acid.

9. A method of treating a patient suffering from a gastric or gastroduodenal disease accompanied by gastric hyperacidity comprising administering to said patient a gastric acid secretion inhibiting and cytoprotecting effective amount of a compound as defined in claim 1.

10. A method of treating a patient suffering from a gastric or gastroduodenal disease accompanied by gastric hyperacidity comprising administering to said patient a gastric acid secretion inhibiting and cytoprotecting effective amount of a compound as defined in claim 2.

11. A method of treating a patient suffering from a gastric or gastroduodenal disease accompanied by gastric hyperacidity comprising administering to said patient a gastric acid secretion and cytoprotecting inhibiting effective amount of a compound as defined in claim 3.

12. A method of treating a patient suffering from a gastric or gastroduodenal disease accompanied by gastric hyperacidity comprising administering to said patient a gastric acid secretion and cytoprotecting inhibiting effective amount of a compound as defined in claim 4.

13. A method of treating a patient suffering from a gastric or gastroduodenal disease accompanied by gastric hyperacidity comprising administering to said patient a gastric acid secretion inhibiting and cytoprotecting effective amount of a compound as defined in claim 5.

14. A method of treating a patient suffering from a gastric or gastroduodenal disease accompanied by gastric hyperacidity comprising administering to said patient a gastric acid secretion inhibiting and cytoprotecting effective amount of a compound as defined in claim 6.

15. A method of treating a patient suffering from a gastric or gastroduodenal disease accompanied by gastric hyperacidity comprising administering to said patient a gastric acid secretion inhibiting and cytoprotecting effective amount of a compound as defined in claim 7.

16. A method of treating a patient suffering from a gastric or gastroduodenal disease accompanied by gastric hyperacidity comprising administering to said patient a gastric acid secretion inhibiting and cytoprotecting effective amount of a compound as defined in claim 8.

17. The method according to claim 9, 10, 11, 12, 13, 14, 15 or 16, wherein the patient treated is suffering from hyperchlorhydria.

18. The method according to claim 9, 10, 11, 12, 13, 14, 15 or 16, wherein the patient treated is suffering from gastric ulcer or gastroduodenal ulcer.

19. The method according to claim 9, 10, 11, 12, 13, 14, 15 or 16, wherein the patient is suffering from gastritis.

20. The method according to claim 9, 10, 11, 12, 13, 14, 15 or 16, wherein the patient treated is suffering from hiatal hernia.

* * * * *